United States Patent
Geissen et al.

(10) Patent No.: US 6,390,167 B1
(45) Date of Patent: May 21, 2002

(54) METHOD AND APPARATUS FOR PRODUCING MULTI-LAYER HYGIENE PRODUCTS

(75) Inventors: Armin Geissen, Melsbach; Albert Becker, Strassenhaus; Hans Peter Buentgen, Andernach; Anja Wilms, Melsbach; Konrad Zilles, Andernach; Hans Werner Soehn, Ochtendung, all of (DE)

(73) Assignee: Winkler & Duennebier AG, Neuwied (DE)

( * ) Notice: Subject to any disclaimer, the term of this patent is extended or adjusted under 35 U.S.C. 154(b) by 0 days.

(21) Appl. No.: 09/382,721

(22) Filed: Aug. 25, 1999

(30) Foreign Application Priority Data

Aug. 25, 1998 (DE) .......................................... 198 38 494

(51) Int. Cl.⁷ .............................................. B32B 31/08
(52) U.S. Cl. ........................ 156/467; 156/502; 156/510; 156/553; 156/578; 156/219; 156/227; 156/250; 156/304.1; 156/324
(58) Field of Search ................................ 156/467, 570, 156/578, 553, 324, 219, 227, 250, 304.1, 502

(56) References Cited

U.S. PATENT DOCUMENTS

| | | | |
|---|---|---|---|
| 3,607,578 A | | 9/1971 | Berg et al. |
| 3,935,047 A | * | 1/1976 | Shinomura .................. 156/242 |
| 3,984,272 A | | 10/1976 | Teed |
| 4,657,802 A | * | 4/1987 | Morman ...................... 428/152 |
| 4,783,231 A | * | 11/1988 | Raley .......................... 156/167 |
| 5,447,590 A | * | 9/1995 | Gilpatrick .................... 156/178 |
| 5,589,258 A | * | 12/1996 | Maddern et al. ............ 428/286 |

* cited by examiner

Primary Examiner—Sam Chuan Yao
(74) Attorney, Agent, or Firm—W. F. Fasse; W. G. Fasse

(57) ABSTRACT

In a method and an apparatus for manufacturing multi-layered hygiene products, a starting material web (2) is transported from one or more supply stations (4) to one or more processing stations (3) in which the starting material is cut, shaped, laminated, folded, etc. so as to form the finished hygiene products. The processing stations (3) are arranged on a processing plane (12), while the supply stations (4) are arranged on a supply plane (13), wherein these two planes are respective parallel vertical planes that are horizontally spaced apart from each other. The physical separation of the supply stations from the processing stations allows an effective noise shielding of the processing stations and the use of larger supply rolls in the supply stations, as well as improved accessibility of the equipment.

27 Claims, 5 Drawing Sheets

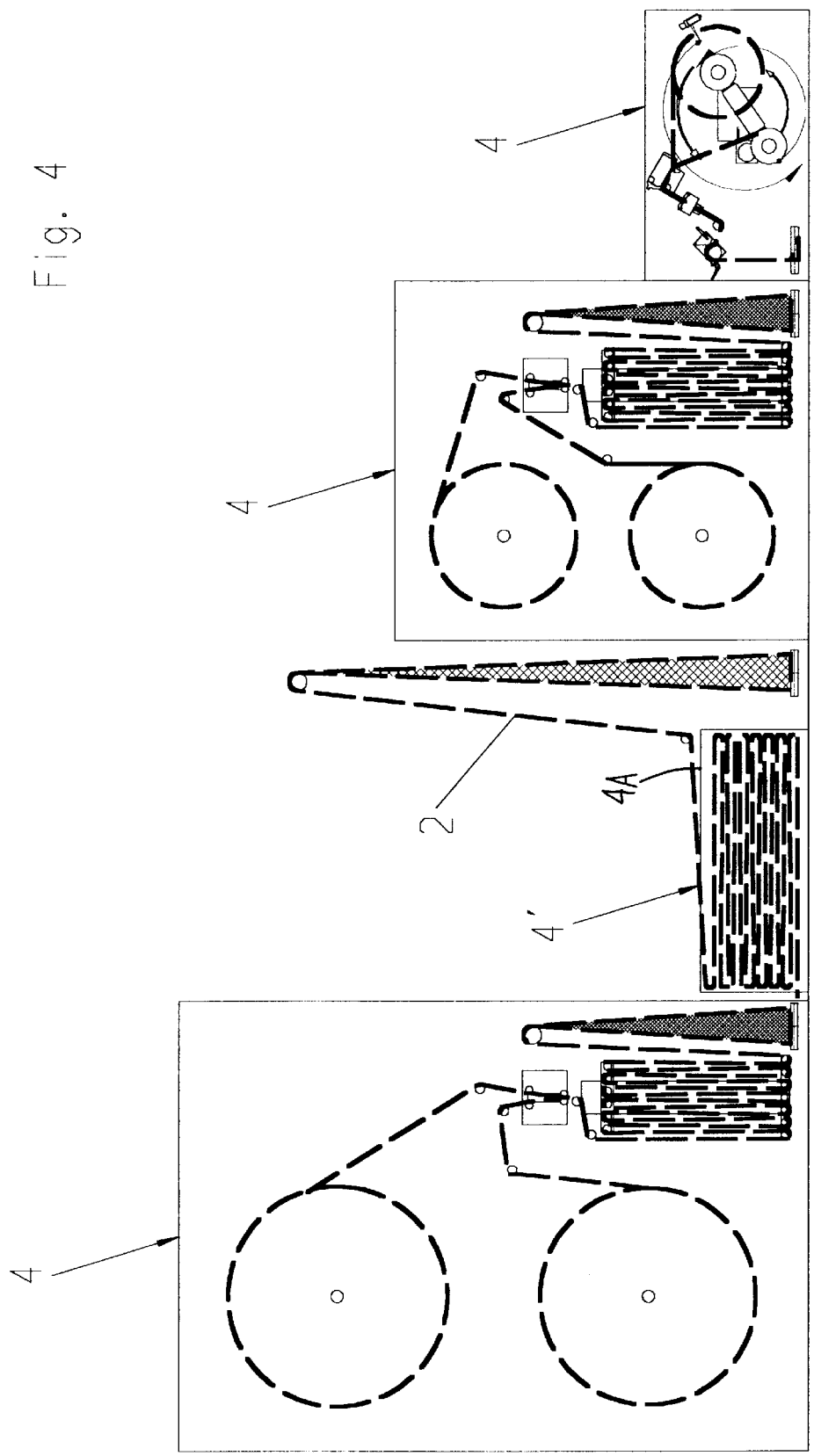

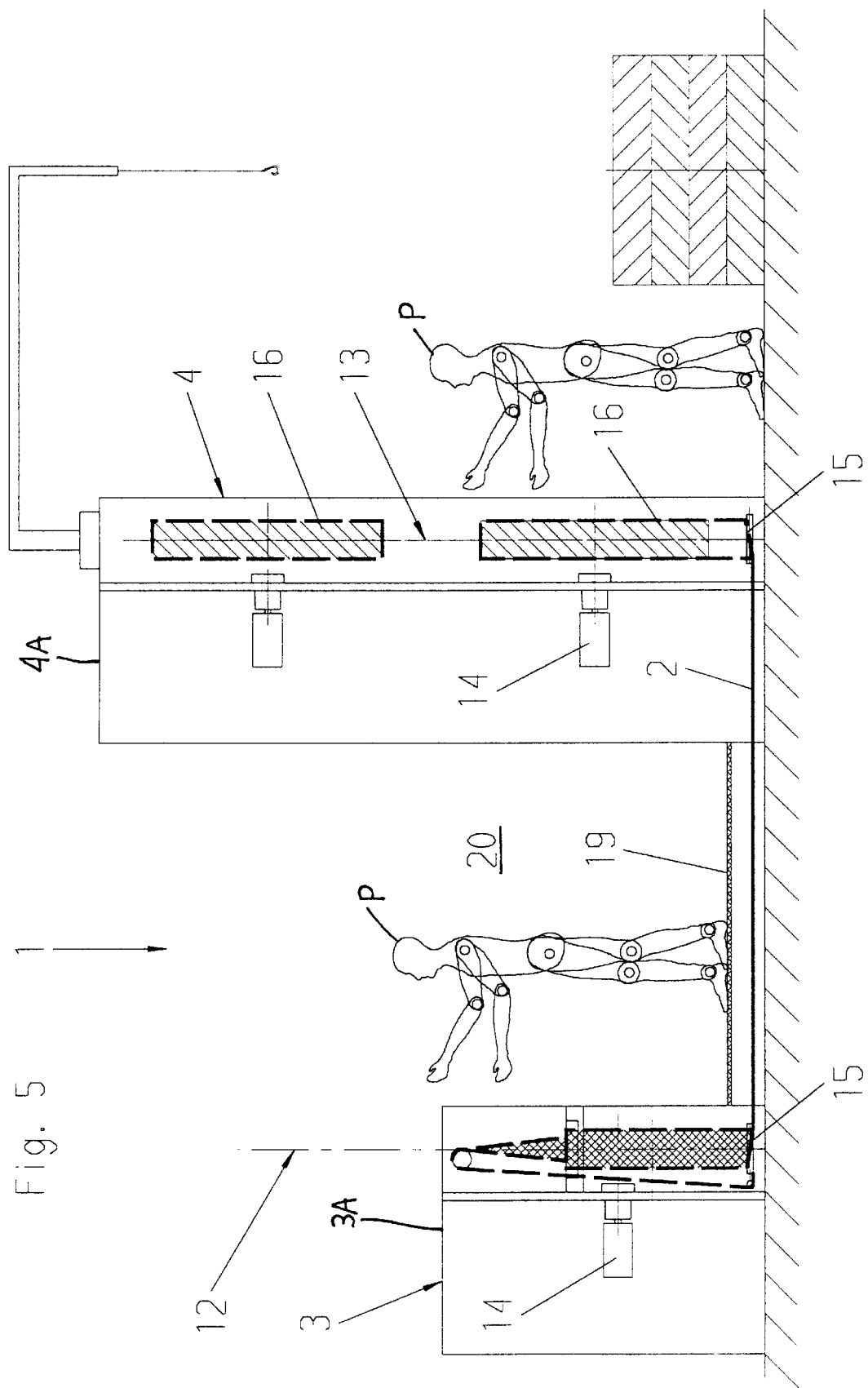

METHOD AND APPARATUS FOR PRODUCING MULTI-LAYER HYGIENE PRODUCTS

PRIORITY CLAIM

This application is based on and claims the priority under 35 U.S.C. §119 of German Patent Application 198 38 494.7, filed on Aug. 25, 1998, the entire disclosure of which is incorporated herein by reference.

FIELD OF THE INVENTION

The invention relates to a method and an apparatus for producing multi-layer hygiene products from various generally web-shaped starting materials forming the individual layers of the finished products, whereby the starting materials are supplied from material supply stations and processed in processing stations to form the finished products.

BACKGROUND INFORMATION

Methods and apparatus of the above mentioned general type are known in the art and are used for producing feminine hygiene pads, liners and shields, sanitary napkins, incontinence pads, liners, shields, panties, and the like, as well as baby diapers and the like, for example. Such modern hygiene products of this type generally comprise several parts and several layers that are connected together in a sandwiched or layered structure. For this purpose it is typical to supply narrow webs or bands of various starting materials from large supply rolls to the actual processing stations in which the starting materials are processed in a suitable manner to form the finished products.

Generally, the supply roll arrangements for supplying the web-shaped starting materials are arranged above the processing stations so that they are easily accessible, and so that successive web-shaped materials can be supplied and seamlessly spliced into the processing sequence from new supply rolls without problems when a prior supply roll has been exhausted. Although the known arrangements with the supply rolls above the processing stations are made as compact as possible, these known arrangements are still often more than 15 meters and up to 20 meters long and very tall.

Generally, the above mentioned apparatus are extremely noisy during operation. In fact, they generate such a level of noise that they must be enclosed in order to reduce the externally emitted noise level. Due to the large size of the overall apparatus arrangement, the noise abatement enclosures or housings are also very large and become inefficient and expensive. Moreover, since the supply stations as well as the processing stations must be housed within the enclosures in the prior art arrangements, the enclosures must have large access doors or flaps through which empty supply rolls may be replaced by new full supply rolls. In view of the high operating speed of the modern apparatus of this type, the material supply provided by the supply rolls is relatively quickly exhausted. Thus, after a relatively short time it will again be necessary to open the enclosure access doors in order to carry out another replacement of the now-empty supply rolls. This, of course, leads to the undesirable emission of noise, and extra complexity and extra work steps in the overall operation of the apparatus.

During each exchanging of the supply rolls it is necessary to temporarily reduce the operating speed of the entire apparatus, to ensure a problem-free splicing of the head or lead end of the web-shaped material of the respective next supply roll onto the tail end of the material supplied by the previous, almost-empty supply roll. Nonetheless, it remains necessary to remove or reject and then dispose of or recycle and reprocess a certain number of the products produced during the transition period when a supply roll exchange is carried out, because these products are likely to have defects resulting from the switch and splicing of the supply material.

SUMMARY OF THE INVENTION

In view of the above, it is an object of the invention to improve an apparatus and a method for producing multi-layer hygiene products, such that the apparatus can operate at the highest possible operating speed and output capacity for the longest possible periods of time without slow-downs or interruptions, whereby it is necessary to utilize material supply rolls having the largest possible diameter. Furthermore, it is an object of the invention to minimize the waste and reject rate of products and of the various starting materials per work shift. Also, the manpower necessary for operating and monitoring the apparatus should be as low as possible. The invention further aims to avoid or overcome the disadvantages of the prior art, and to achieve additional advantages, as apparent from the present specification.

The above objects have been achieved in a method and an apparatus for producing multi-layered hygiene products, according to the invention, wherein plural starting materials which are generally in a web shape are supplied from material supply stations to a plurality of processing stations in which the starting materials are processed as required, e.g. by being embossed, supplied with an adhesive, bonded together, cut and folded to appropriate sizes and shapes, and the like, in order to form the finished hygiene products. Particularly according to the invention, the at least one processing station used for producing the finished products is spatially separated from the at least one material supply station by respectively arranging the processing station and the supply station in separate parallel planes. More particularly, these separate parallel planes, namely a processing plane and a supply plane, are respective vertical planes that are spaced apart from each other in a horizontal direction. Thus, the one or more material supply stations and the one or more processing stations are arranged laterally next to one another with a passage aisle or alley therebetween, in a preferred arrangement.

Basically according to the invention, at least one, but preferably as many as possible or all of the material supply rolls of the supply station are arranged on the supply plane which is separate and parallel relative to the processing plane on which are arranged the processing stations serving for the production of the hygiene products. By separating the supply rolls from the processing stations in this manner, it is possible to provide a noise abatement enclosure or housing around the noise-generating processing stations, whereby this enclosure or housing substantially encloses the entire processing stations continuously during the operation of the apparatus. In this context, "substantially enclosing" means enclosing a predominant portion (e.g. at least 90%) of the top and all sides of the processing equipment.

On the other hand, the supply stations including the supply rolls typically generate a very low level of noise, and so these supply stations do not need to be enclosed for noise abatement purposes at all. Instead, only simple worker safety enclosures or guards are provided around the supply stations for the protection of the operating personnel. By thus separating the supply stations from the processing stations, and keeping the supply stations outside of the noise abatement enclosure of the processing stations, it is no longer necessary to repeatedly open the noise enclosure for the purpose of switching supply rolls. Also, the noise abatement enclosure can be made smaller and thereby more effective for its noise abatement purpose as well as more economical.

Moreover, with the present inventive arrangement, the supply rolls arranged on their own separate supply plane can be made larger than typical prior art supply rolls, because these supply rolls do not need to fit inside a noise abatement enclosure. In this manner, the larger supply rolls provide a longer continuous supply of material, and the operating time during which the apparatus can be operated at the highest output speed between exchanges of the supply rolls can be increased. Consequently, it is possible to reduce the amount or rate of reject products and also to increase the production output per work shift, because the apparatus suffers less down time and slow-downs due to supply roll exchanges.

These benefits are particularly achieved in connection with a complete separation between the processing plane on which the processing stations are arranged and the supply plane in which the starting material is stored on respective supply rolls of the supply stations. In other words, preferably all of the various material supply arrangements (including supply rolls supplying web-shaped materials and other supply means supplying non-web materials) included in the apparatus are arranged together on the supply plane, and all of the processing equipment is arranged together on the processing plane.

It is further advantageous if the starting material is guided generally along or near the floor, from the supply plane to the processing plane. This can be carried out in a supply channel or under a floor platform arranged between the supply plane and the processing plane. It should also be understood that such an advantageous arrangement is not limited to the supply of web-shaped starting materials. To the contrary, starting materials that are not web-shaped also can be transported along or near the floor from the supply plane to the processing plane through an appropriate channel or transport arrangement such as a conveyor arrangement.

Nonetheless, the invention is not limited to a transport of the starting material along or near the floor. Instead, the starting material can be transported overhead or along or near the ceiling for example, between the supply plane and the processing plane.

Various types of starting materials, including starting materials that are not in a web-form and that are therefore not stored on supply rolls, can be supplied from appropriate supply stations that are also arranged on the supply plane. Such non-web-shaped starting materials include flaky or flocculent materials, super absorbent materials comprising absorbent swelling substances based on acrylic or cellulose materials for example, deodorant substances, odor blocking or masking substances, binders, glues and/or adhesives, or the like.

For supplying web-shaped starting materials from supply rolls, it should be noted that the supply rolls themselves can be arranged either parallel or perpendicular relative to the supply plane and relative to the processing plane, with suitable transport and guide arrangements so that the web-shaped starting material can be rolled from the supply roll and then driven and deflected as necessary to be supplied from the supply roll to the processing stations in the processing plane.

BRIEF DESCRIPTION OF THE DRAWINGS

In order that the invention may be clearly understood it will now be described in connection with an example embodiment, with reference to the drawings, wherein:

FIG. 3 shows a supply station in a supply plane of the apparatus;

FIG. 4 is a schematic side view of an alternative embodiment of the apparatus, showing different supply stations in the supply plane; and FIG. 5 is a schematic sectional view through the entire apparatus, including a processing station in its processing plane, and a supply station in its supply plane.

Figure 1:
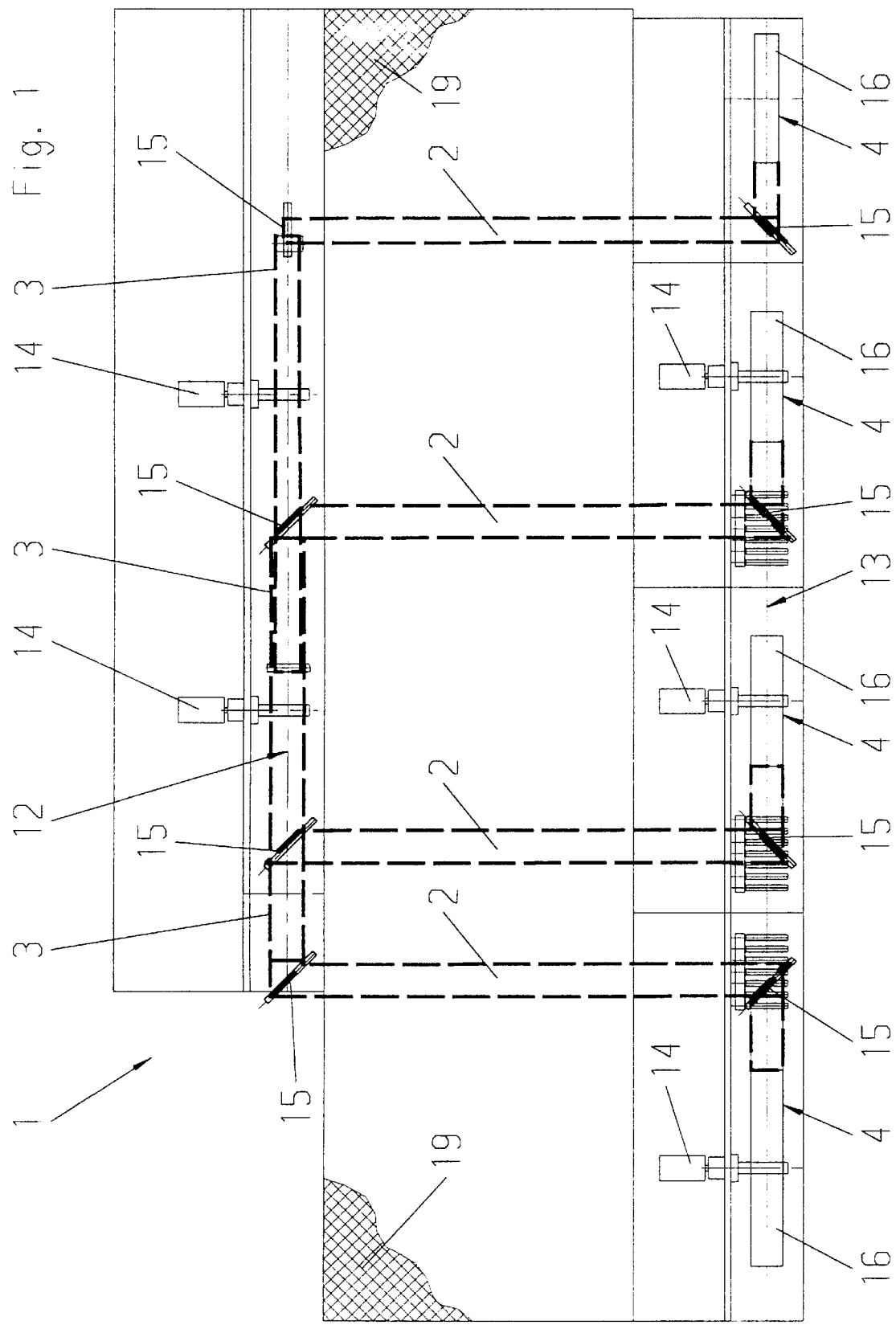
FIG. 1 is a schematic top view of the overall layout of an apparatus according to the invention.

DETAILED DESCRIPTION OF PREFERRED EXAMPLE EMBODIMENTS AND OF THE BEST MODE OF THE INVENTION

An apparatus 1 for manufacturing multi-layered hygiene products generally comprises a plurality of processing stations 3 as well as a plurality of supply stations 4. The supply stations 4 generally supply web-shaped starting materials 2 or also other starting materials that are not web-shaped, which respectively form the individual layers and parts of the finished hygiene products. The starting materials 2 supplied by the supply stations 4 are transported to the processing stations 3 where the materials are processed to form the finished hygiene products.

More particularly, the processing stations 3 may include embossing or stamping stations 5 and 6 as well as a cutting station 7 for respectively embossing, quilting or stamping and cutting the starting material in the process of manufacturing the hygiene products. The apparatus further includes transport arrangements 8 for transporting the material through the processing stations, adhesive applicator devices 9 for applying glue or other adhesives onto the materials forming the hygiene products, as well as a web guidance arrangement 10 for guiding the web of material among the respective processing stations. The material supply stations 4 include supply equipment as will be described below, for example. Various drive devices 14 and deflector devices 15 for driving and guiding the web-shaped starting material 2 are arranged in association and cooperation with both the processing stations 3 and the supply stations 4.

The details of the construction and operation of the various processing stations, supply stations and other equipment for handling the web-shaped and other starting materials are not particularly limited in the context of the present invention. Namely, these various material supply stations, processing stations and material handling devices can be in accordance with any conventional construction and operation.

The basic underlying feature of the apparatus according to the invention is the complete or predominant spatial and physical separation of the processing stations 3 that serve for producing the hygiene products from at least one supply station 4 that supplies the web-shaped starting material 2. This is achieved by arranging the processing stations 3 and the material supply station or stations 4 respectively on separate parallel planes 12 and 13, namely a processing plane 12 and a supply plane 13. Preferably, the processing plane 12 and the supply plane 13 are respective vertical planes arranged laterally or horizontally spaced apart from one another, as shown particularly in FIGS. 1 and 5.

The web-shaped starting material 2 is initially supplied and stored in a condition rolled-up on supply rolls 16 in the supply stations 4. From there, the web-shaped starting material 2 runs from the supply rolls 16 through a material web store or reserve 17, which may have any conventional construction and operation. Moreover, a respective web end splicer device 18 is arranged between the supply roll 16 and the material web store or reserve 17, for splicing the head or lead end of a new web of starting material to the tail end of the prior web of starting material. Downstream from the material web store or reserve 17, as seen in the material transport direction, the web-shaped starting material 2 is transported to a deflector device 15 arranged generally near or along the floor, i.e. near the bottom of the material web store or reserve 17, as shown especially in FIGS. 3 and 5.

Figure 2:
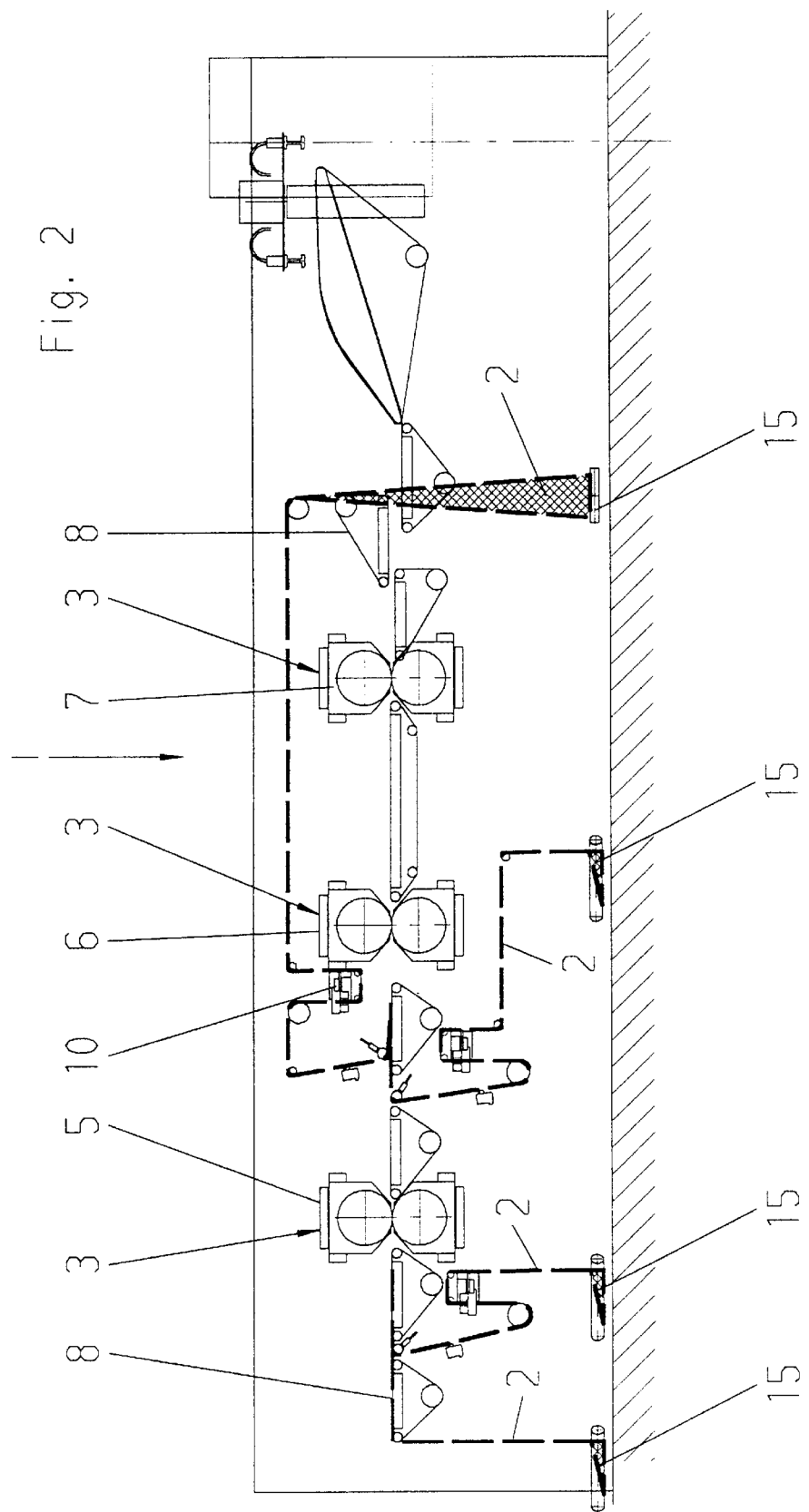
FIG. 2 is a schematic side view showing various processing stations in the processing plane of the apparatus.

From the just mentioned deflector device 15, which forms a part of each respective supply station 4, the web-shaped starting material 2 is transported generally near or along the floor in a transport channel or under a floor platform 19 or the like. Such a floor platform 19 forms a walkway for the operating personnel P, between the supply stations 4 and the processing stations 3, as shown in FIG. 5. After traversing under the floor platform 19, the web-shaped starting material 2 is guided and deflected over a respective deflector device 15 generally at the bottom of the processing station 3 as shown in FIGS. 2 and 5.

Thus, between the deflector device 15 of each material supply station 4 and the deflector device 15 of each processing station 3, the respective web-shaped material 2 spans the spacing distance between the supply plane 13 and the processing plane 12 underneath the floor platform 19. The platform 19 is arranged in a passage or access alley 20 between the processing stations 3 and the supply stations 4. This allows convenient access to all of the equipment of the processing stations 3 and the supply stations 4 by the operating personnel P.

The inventive arrangement also allows a compact noise abatement housing or enclosure 3A to substantially completely enclose and encapsulate the processing stations 3 (except for the openings near the deflector devices 15 through which the material 2 enters into the processing stations 3), without having to provide openable access flaps or doors for accessing and exchanging the supply rolls 16 therein. On the other hand, the larger arrangement of the supply stations 4 can be partially or completely enclosed in a safety enclosure 4A, which does not need to have sound insulating properties in view of the much lower noise generation of the material supply stations 4.

Figure 3:
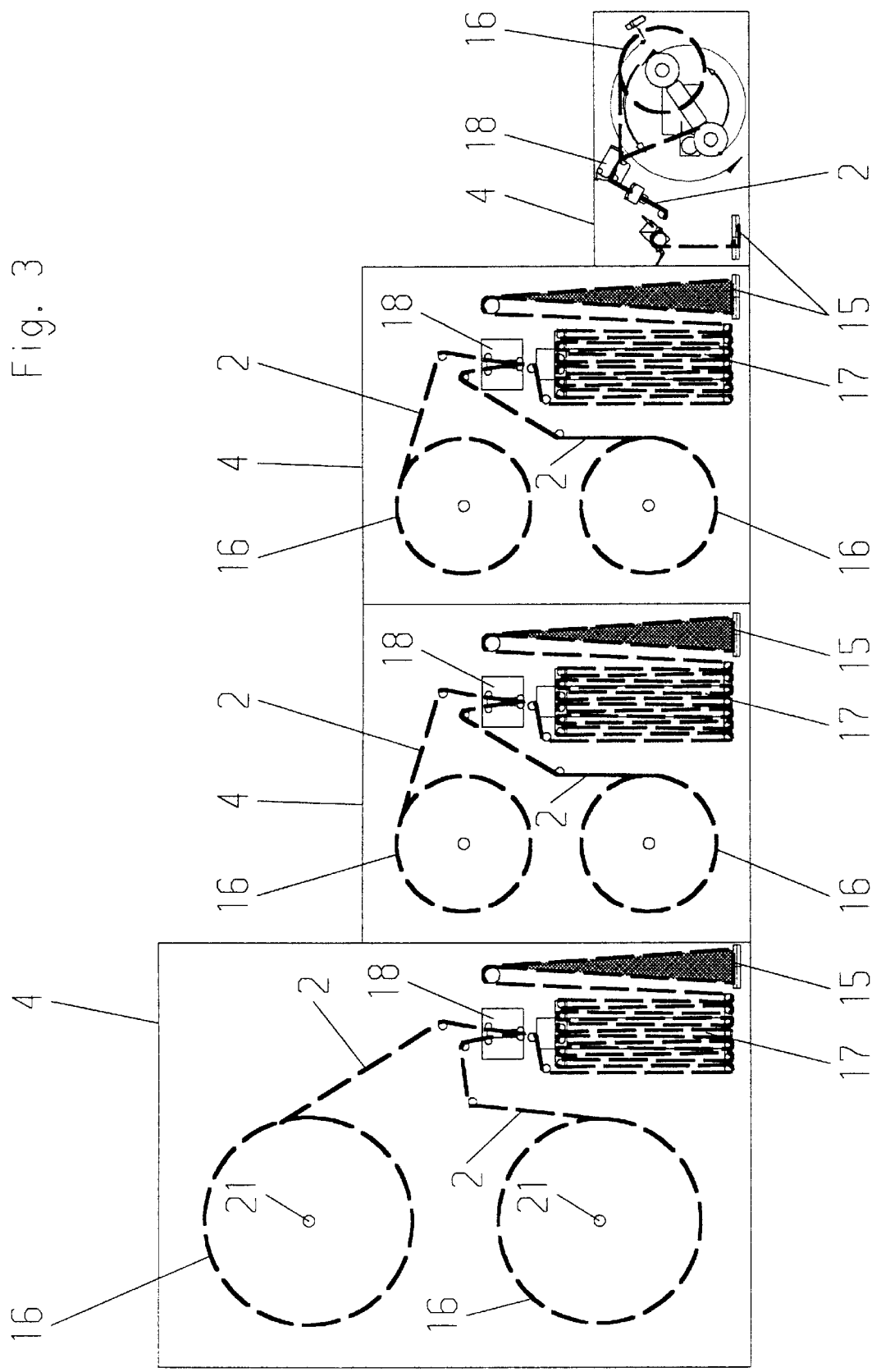
FIG. 3 is a schematic side view of the apparatus from an opposite side relative to that of FIG. 2, whereby

FIG. 3 schematically illustrates a first embodiment of plural supply stations 4 arranged on the supply plane 13. As shown in FIG. 3, one especially large supply station 4 includes two very large supply rolls 16 of web-shaped starting material 2, while two smaller supply stations 4 respectively include two smaller supply rolls 16. As an example, if the two smaller supply stations 4 represent the size of supply rolls 16 that can be maximally used in conventional arrangements, the largest supply station 4 represents the larger size of supply rolls 16 that can now be used according to the invention. In any event, in each of these supply stations, the starting material 2 is supplied from one of the rolls until the material supply from this roll is depleted, and then the head or lead end of the web of material 2 from the other supply roll 16 will be spliced to the tail end of the exhausted web of starting material by the web end splicer device 18 before being supplied into the store or reserve 17. The right side of FIG. 3 shows a still smaller supply station 4 with an alternative arrangement of revolving small supply rolls 16 from which the material web is similarly fed through a splicer device 18. As mentioned above, all of these supply stations may have any known arrangement and construction of the supply equipment.

FIG. 4 shows another alternative embodiment of supply stations 4 arranged on the supply plane 13. The embodiment according to FIG. 4 includes the same supply stations 4 at the first, third, and fourth positions (as counted from the left) as the embodiment in FIG. 3. However, the second supply station (as counted from the left) has a different configuration. Namely, this different supply station 4' uses a material supply box 4A to supply a folded or pleated stack of supply material, instead of the provision of supply rolls 16 to supply the continuous web of starting material 2. Such material supply boxes 4A are generally known in the art, and can be used in the apparatus according to the invention.

The invention is not limited to particular processing stations 3 or supply stations 4 or 4'. Instead, the essential feature of the inventive apparatus 1 is that the processing plane 12 and the supply plane 13 are arranged next to one another and particularly parallel next to one another. An individual processing station 3 or plural processing stations 3 or a group of processing stations 3 is arranged on the processing plane 12, while separately therefrom, individual, plural or grouped supply stations 4 or 4' are located on the supply plane 13. In this context, it should be understood that the respective equipment is not strictly and structurally arranged and limited to a particular plane. For example, all of the processing station equipment does not have to be strictly arranged in a coplanar fashion directly along the processing plane 12. The same holds true for the arrangement of the supply stations 4 and 4' on the supply plane 13. The various different stations do not even need to be strictly coplanar with each other. Instead, the "processing plane" and "supply plane" merely refer to a conceptual plane that virtually extends through the major components of the respective equipment. Preferably, the major axes of the equipment are generally aligned in common along the respective planes.

The illustrated embodiments all relate to the situation in which the supply rolls 16 are oriented with their respective rotation axes 21 perpendicular to the supply plane 13. The several supply stations 4 are arranged in a row one after the other along the supply plane 13. In this case, the row of supply stations 4 defines the supply plane 13, which extends substantially parallel to and horizontally spaced from the processing plane 12, which in turn is defined by the similar rowed arrangement of the processing stations 3 one behind the other. The rotation plane of the supply rolls thus coincides with or extends parallel to the supply plane and parallel to the processing plane. It should be understood, however, that all or some of the supply stations 4 can be arranged at an angle such as a right angle relative to the supply plane 13 and thus also relative to the processing plane 12 defined by the processing stations 3. Even with such an arrangement, all or at least some of the supply stations 4 will be arranged on a plane, namely the supply plane 13, which is distinct from and spaced apart from the processing plane 12 defined by the processing stations 3.

While the above examples relate to the supply of a web-shaped starting material 2, it should be understood that the starting material can have any other configuration, and is not limited to a continuous web configuration. Namely, any conventionally known transport equipment for transporting individual precut blanks of material or the like can be used to transport the starting material from a supply plane 13 to a processing plane 12.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. An apparatus for producing multi-layered hygiene products, comprising:
   a first supply station adapted to include a supply amount of a material and to supply the material to be used in making the hygiene products;
   a plurality of processing stations including at least a cutting device and a folding device adapted to receive and process the material to make the hygiene products; and
   a transport arrangement arranged and adapted to transport the material from said first supply station to said processing stations;
   wherein said first supply station is arranged on a vertical supply plane that extends through said first supply station and does not extend through said processing stations, and said processing stations are all arranged on a vertical processing plane that extends through said processing stations and does not extend through said first supply station, and that is parallel to and horizontally spaced apart from said supply plane; and
   wherein said first supply station is spatially separated and distinct from said processing stations.

2. The apparatus according to claim 1, wherein said first supply station comprises a rotatable mounting axle adapted to receive thereon a supply roll containing a web of the material and wherein said supply plane extends through said rotatable mounting axle.

3. The apparatus according to claim 2, wherein a rotation axis of said rotatable mounting axle is parallel to said supply plane.

4. The apparatus according to claim 2, wherein a rotation axis of said rotatable mounting axle is perpendicular to and perpendicularly intersects said supply plane.

5. The apparatus according to claim 4, wherein said rotatable mounting axle is centrally bisected by said supply plane.

6. The apparatus according to claim 2, wherein a rotation axis of said rotatable mounting axle lies in and extends along said supply plane.

7. The apparatus according to claim 1, wherein said first supply station and said processing stations are entirely horizontally spaced apart from each other with an unobstructed spacing distance therebetween sufficiently large to allow a person to pass therethrough.

8. The apparatus according to claim 7, further comprising a floor platform with a transport space therebelow, arranged to span said spacing distance between said first supply station and said processing stations, and
   wherein said transport arrangement is arranged at least partially below said floor platform so as to transport the material from said first supply station to said processing stations through said transport space below said floor platform.

9. The apparatus according to claim 1, further comprising a noise abatement enclosure having noise attenuating properties and substantially entirely enclosing at least one of said processing stations, without enclosing said first supply station.

10. The apparatus according to claim 9, comprising a plurality of supply stations including said first supply station, wherein all of said processing stations are arranged entirely within said noise abatement enclosure and all of said supply stations are arranged entirely outside of said noise abatement enclosure.

11. The apparatus according to claim 1, comprising a plurality of supply stations including said first supply station arranged in a first row one behind another, wherein said processing stations are arranged in a second row one behind another parallel to said first row, and wherein said supply plane is defined as extending along said first row and said processing plane is defined as extending along said second row.

12. The apparatus according to claim 1, wherein:
   said processing stations further comprise at least one of an adhesive applicator device, an embossing device, and a laminator device;
   said first supply station comprises at least one of a material web supply roll, a material supply box, a web splicer, a material reserve arrangement, a material deflection roll, a material deflection shaft, and a material drive roll; and
   said transport arrangement comprises a first deflection device arranged at a bottom of said first supply station and a second deflection device arranged at a bottom of a first one of said processing stations.

13. The apparatus according to claim 1, further comprising a second supply station adapted to include a second supply amount of a second material and to supply the second material to be used in making the hygiene products.

14. The apparatus according to claim 13, wherein said second supply station is arranged on said supply plane which extends through both said first and second supply stations, and wherein said processing plane does not extend through said second supply station.

15. The apparatus according to claim 1, wherein said processing stations are arranged so that the material will move through and between said processing stations along a processing path that is parallel to or lies on said processing plane.

16. The apparatus according to claim 1, wherein said processing plane is defined as being located so as to extend along a longitudinal center line of the material being processed in said processing stations.

17. The apparatus according to claim 1, wherein said first supply station is arranged so that the material will move in said first supply station and from said first supply station to said transport arrangement along a supply path that is parallel to or lies on said supply plane.

18. The apparatus according to claim 1, wherein said supply plane is defined as being located so as to extend along a longitudinal center line of the material being supplied in said first supply station.

19. A method of using the apparatus according to claim 1, for producing multi-layered hygiene products, comprising the following steps:
   a) supplying a web-shaped first material from said first supply station at said supply plane;
   b) transporting said first material from said first supply station at said supply plane to a first one of said processing. stations at said processing plane using said transport arrangement; and
   c) processing said first material in said processing stations at said processing plane so as to produce said multi-layered hygiene products from at least said first material.

20. The method according to claim 19, wherein the apparatus further includes a second supply station, and further comprising supplying a non-web-shaped second material from said second supply station also on said supply plane, transporting said second material from said supply plane to said processing plane, and processing said second material together with said first material to produce said multi-layered hygiene products.

21. The method according to claim 20, wherein said second material is not stored on or supplied from a supply roll and comprises a material selected from the group consisting of flaky materials, flocculate materials, super absorbent materials containing swelling agents based on acrylic or cellulose, deodorizing agents, odor masking agents, binders and adhesives.

22. The method according to claim 19, wherein all material supply rolls of said apparatus are supported and unrolled on said supply plane separate from said processing plane.

23. The method according to claim 19, further comprising maintaining a complete separation between said supply plane and said processing plane, except for said transporting of said material from said supply plane to said processing plane.

24. The method according to claim 19, wherein said transporting of said material is carried out adjacent to a floor below said first supply station and said processing stations.

25. The method according to claim 19, wherein said transporting of said material is carried out overhead above said first supply station and said processing stations.

26. The method according to claim 19, wherein said supplying comprises rolling said material off a supply roll arranged parallel to said processing plane.

27. The method according to claim 19, wherein said supplying comprises rolling said material off a supply roll arranged perpendicular to said processing plane.

* * * * *